United States Patent [19]

Capiris et al.

[11] Patent Number: 5,464,855
[45] Date of Patent: Nov. 7, 1995

[54] THIOPHENE-2-CARBOXAMIDOTETRAZOLES AND PHARMACEUTICAL USE THEREOF

[75] Inventors: Thomas Capiris, Plymouth; David T. Connor, Ann Arbor, both of Mich.

[73] Assignee: Warner-Lambert Company, Morris Plains, N.J.

[21] Appl. No.: 287,572

[22] Filed: Aug. 9, 1994

[51] Int. Cl.$^6$ .................... C07D 403/12; C07D 495/04; A61K 31/44; A61K 31/41
[52] U.S. Cl. .................... 514/382; 514/252; 546/114; 548/252
[58] Field of Search ............................ 548/252; 514/382, 514/301; 546/114

OTHER PUBLICATIONS

*The Journal of Immunology*, vol. 144, No. 7, Apr. 1990; Shappell et al., pp. 2702–2711.
*Journal of Leukocyte Biology*, vol. 48, 1990, Rosen, pp. 465–469.
*The Journal of Immunology*, vol. 150, No. 6, Mar. 1993, Mulligan et al., pp. 2401–2406.
*Circulation*, vol. 81, No. 1, Jan. 1990, Simpson et al., pp. 226–237.
*Gastroenterology*, vol. 100, No. 4, 1991, Wallace et al., pp. 878–883.
*American Journal of Physiology*, vol. 259, 1990, Wallace et al., pp. G462–G467.

*Primary Examiner*—David B. Springer
*Attorney, Agent, or Firm*—Charles W. Ashbrook

[57] ABSTRACT

Thiophene-2-carboxamidotetrazoles inhibit the Mac-1 integrin and are thus useful for treating diseases mediated by Mac-1 adhesion, including inflammatory disorders.

28 Claims, No Drawings

THIOPHENE-2-CARBOXAMIDOTETRAZOLES AND PHARMACEUTICAL USE THEREOF

BACKGROUND OF THE INVENTION

This invention relates thiophene-2-carboxamidotetrazoles which inhibit the effects of the Mac-1 leukocyte molecule, and as such are useful for treating diseases mediated thereby, including inflammatory disorders.

Leukocyte-endothelial interactions are involved in the pathogenesis of various inflammatory diseases. In an immune or inflammatory response, circulating neutrophils interact with the endothelium via their adhesion molecules. The adherence of the neutrophil to the endothelium, and the subsequent transendothelium migration to the site of injury or infection, is the normal host response. Unfortunately, in various disease states such a response can become too aggressive; the influx of neutrophils can cause damage to tissue, thereby causing chronic inflammation.

Cell adhesion molecules can be classified in a number of families, three of which are the integrins, the immunoglobulins, and the selectins. The integrins can be found on leukocytes and platelets. They bind to the immunoglobulin family on blood vessel endothelial cells.

The leukocyte adhesion molecule Mac-1 (CD11b/CD18) is a heterodimeric glycoprotein expressed on the plasma membrane of neutrophils and monocytes. Mac-1 is a member of the $\beta_2$ subfamily of integrins. Interaction of upregulated Mac-1 on stimulated neutrophils with its ligands on endothelial cells plays an important role in the pathogenesis of numerous inflammatory disease states. The response of the neutrophil in host defense function depends on this type of adherence. The inflammatory response depends on neutrophil influx to the site of infection or injury. A rational target for therapeutic intervention thus is to inhibit the adhesion process. Drugs which inhibit the adhesion of leukocytes to the endothelium could be used as therapeutic agents in such conditions as ischemia, reperfusion, transplant rejection, ulcerative colitis, inflammatory bowel disease, multiple sclerosis, rheumatoid arthritis, and NSAID-induced gastropathy.

The binding of the denatured protein known as keyhole limpet hemocyanin (KLH) to human and canine neutrophils has been shown to be Mac-1 specific (*J. Immunol.*, 144(7):2702–2711, April 1990). The binding of stimulated neutrophils (with fMLP) to KLH can be blocked with antibodies to Mac-1. An inhibition of the adhesion process using monoclonal antibodies has been shown to inhibit the inflammatory response in a model of lung injury (Rosen H., *J. Leuk. Biol.*, 48–465 (1990); Mulligan M. S., et al., *J. Immunol.*, 150:2401–2406 (1993)), and a canine model of myocardial ischemia/reperfusion injury (Simpson P. J., et al., *Circulation*, 81:226–237 (1990)). We have now discovered that small molecular weight thiophene-2-carboxamidotetrazoles also inhibit the adhesion of Mac-1 to KLH coated plates.

The role of leukocyte adhesion molecules in NSAID gastropathy has been well documented by John Wallace, et al., *Gastroenterology*, 100:878–883 (1991); *Am. J. Physiol.*, 259:G462–G467 (1990). Neutrophil adherence to the endothelium is a critical pathogenic event in models of gastrointestinal ulceration. Anti-CD18 monoclonal antibody markedly reduced the severity of damage induced by indomethacin in the rat. Similar results were obtained with anti-ICAM. While these monoclonal antibodies have been found to inhibit the adhesion of Mac-1, the need continues to find small molecular weight organic molecules which are also effective. We have now found that the thiophene-2-carboxamidotetrazoles described below inhibit Mac-1 adhesion, and thereby are effective in treating diseases medicated thereby.

An object of this invention is thus to provide new compounds which are characterized as thiophene-2-carboxamidotetrazoles. The invention additionally provides a method for inhibiting the adhesion of Mac-1 in diseases mediated by such molecule. A further object is a method for treating diseases including NSAID-induced gastritis and ulceration, ischemia, reperfusion, ulcerative colitis, inflammatory bowel disease, rheumatoid arthritis, and multiple sclerosis.

SUMMARY OF THE INVENTION

This invention provides new chemical entities which are thiophene-2-carboxamidotetrazoles. The invention provides compounds of Formula I

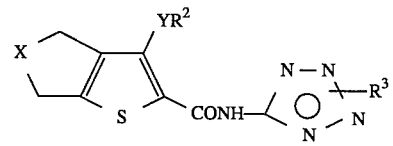

wherein
X is $(CH_2)_{1-2}$,

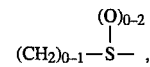

and $(CH_2)_{0-1}$—$NR^1$, where $R^1$ is hydrogen, $C_1$–$C_6$ alkyl, $C_1$–$C_6$ alkanoyl, or $C_1$–$C_6$ alkoxycarbonyl;

Y is O or S;

$R^2$ is $C_1$–$C_6$ alkyl, $(CH_2)_{0-1}$ Ar, where Ar is phenyl or phenyl substituted with one, two, or three groups selected from halo, $C_1$–$C_6$ alkyl, hydroxy, $C_1$–$C_6$ alkoxy, nitro, amino, $C_1$–$C_6$ alkylamino, and di-$C_1$–$C_6$ alkylamino;

$R^3$ is hydrogen, $C_1$–$C_6$ alkyl, $C_2$–$C_6$ alkenyl, and $C_2$–$C_6$ alkynyl;

and the pharmaceutically acceptable salts and solvates thereof.

Preferred compounds have the above formula wherein $R^3$ is hydrogen. Further preferred compounds are those wherein $R^2$ is alkyl, and Y is O. Other preferred compounds are those wherein X is —($CH_2$)$_2$, —($CH_2$)$_{0-1}$—S—, and —($CH_2$)$_{0-1}$NH—.

A further embodiment of this invention is a pharmaceutical formulation comprising a compound of the above Formula I together with a pharmaceutically acceptable carrier, excipient, or diluent therefor. In still another embodiment, the invention provides a method for providing cytoprotection to a subject in need thereof by inhibiting the Mac-1 integrin by administering an effective amount of a compound of Formula I. The invention further provides a method of treating inflammation, NSAID-induced gastritis, NSAID-induced ulceration, ischemia, reperfusion, ulcerative colitis, inflammatory bowel disease, rheumatoid arthritis, and multiple sclerosis comprising administering to a subject an effective amount of a compound of Formula I.

DETAILED DESCRIPTION OF THE INVENTION

In the above formula defining the compounds of this invention, X includes $(CH_2)_{1-2}$,

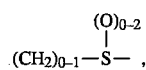

and $(CH_2)_{0-1}-NH^1$, where $R^1$ is hydrogen $C_1-C_6$ alkyl $C_1-C_6$ alkanoyl, or $C_1-C_6$ alkoxycarbonyl. The term "$C_1-C_6$ alkyl" refers to aliphatic carbon chains which are straight or branched and have from 1 to 6 carbon atoms. Typical examples include methyl, ethyl, isopropyl, tert-butyl, 1,2-dimethylbutyl, and the like. "$C_1-C_6$ Alkanoyl" includes formyl, acetyl, propionyl, and butanoyl. Typical "$C_1-C_6$ alkoxycarbonyl" groups include methoxycarbonyl, isopropoxycarbonyl, and tert-butoxycarbonyl (BOC).

$R^2$ in the above formula includes the group $(CH_2)_{0-1}Ar$, where Ar is phenyl or phenyl having up to three substituents The substituents can be "halo" which includes chloro, fluoro, bromo, and iodo. Other substituents include "$C_1-C_6$ alkylamino" groups such as methylamino, ethylamino, isopropylamino, and the like. "Di-$C_1-C_6$ alkylamino" includes dimethylamino, di-n-propylamino, methylethylamino, methylhexylamino, and the like.

$R^3$ in the above formula is defined as hydrogen, $C_1-C_6$ alkyl, $C_2-C_6$ alkenyl, and $C_2-C_6$ alkynyl; The term "$C_2-C_6$ alkenyl" includes ethenyl, 2-butenyl, and 3-pentenyl. Typical "$C_2-C_6$ alkynyl" groups include ethynyl, 3-hexynyl, and the like.

As noted above, X can be $(CH_2)_{1-2}$. When X is —$CH_2$—, the invention compounds are named as cyclopenta[b]thiophenes, and when X is —$CH_2CH_2$—, the invention compounds are cyclohexa[b]thiophenes.

X can also be the group

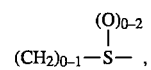

in which case the invention compounds are thienothiopyrans, thienothioxopyrans, and thienothidioxopyrans. Typical compounds include those having the following partial structures:

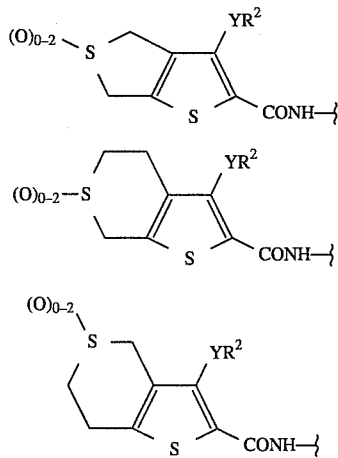

Invention compounds wherein X is $(CH_2)_{0-1}$—$NR^1$ have the following partial structure:

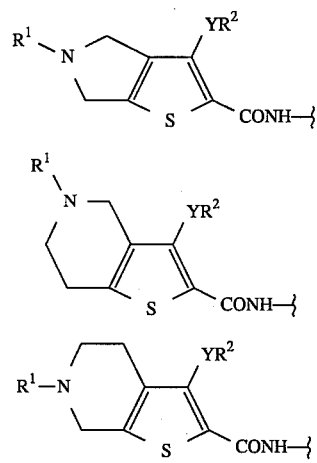

where $R^1$ and $R^2$ are as defined above.

The compounds of the invention can be prepared by coupling a thiophene-2-carboxylic acid or derivative thereof (such as an acid halide, anhydride, or active ester) with an aminotetrazole, according to the following general scheme:

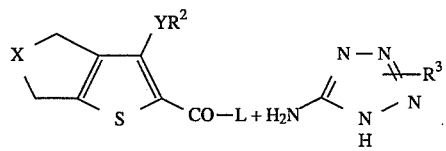

where L is hydroxy or a good leaving group such as halo, for instance chloro, or alkanoyloxy such as formyloxy or acetoxy, or an ester forming group such as pentafluorophenoxy. For example, thiophene-2-carboxylic acids readily react with an aminotetrazole in the presence of a coupling reagent such as those commonly utilized in peptide synthesis, e.g., dicyclohexylcarbodiimide (DCC), carbonyldiimidazole (CDI), and N-ethoxycarbonyl-2-ethoxy-1,2-dihydroquinoline (EEDQ). The direct coupling of a thiophene-2-carboxylic acid with an aminotetrazole is carried out by combining approximately equimolar quantities of the acid and amine in a mutual solvent such as dichloromethane, dimethylformamide, tetrahydrofuran, toluene or the like, and adding about an equimolar amount, or slight excess, of the coupling reagent. The coupling reaction typically is substantially complete within about 24 hours when carried out at a temperature of about 0° to about 30° C. The product, a thiophenecarboxamidotetrazole of the invention, is readily isolated by standard procedures, for instance, filtration and evaporation of reaction solvents, followed by routine purification, if desired, by crystallization from solvents such as methanol or acetone, or chromatography over solid supports such as silica, or the like.

Alternatively, the invention compounds are prepared by routine acylation processes, for instance, by reacting the aminotetrazole with a thiophenecarboxylic acid halide, active ester, or anhydride. The acylation reaction can be accomplished by combining the thiophenecarboxylic acid halide, active ester, or anhydride with about an equimolar quantity of an aminotetrazole in a mutual unreactive organic solvent such as tetrahydrofuran, diethyl ether, dichloromethane, acetone, dioxane, dimethylsulfoxide, benzene, toluene, and the like. If desired, a base can be utilized as an acid scavenger. Commonly used bases include sodium carbonate, pyridine, triethylamine, and the like. The acylation reaction generally is carried out at a temperature of about 20° to about 200° C., preferably from about 30° to about 120° C. The reaction generally is substantially complete within about 2 to 24 hours. The product of the acylation, a thiophene-2-carboxamidotetrazole of the invention, is readily isolated by routine methods, for instance by evaporation of the reaction solvents under reduced pressure. The product can be further purified if desired by chromatography, crystallization, and the like.

The acid halides, active esters, and anhydrides utilized in the acylation reaction are readily prepared by routine methods. For instance, the acid halides are prepared by reacting a thiophene-2-carboxylic acid with a halogenating agent such as thionyl chloride, phosphorus trichloride, phosphorus pentabromide, oxalyl chloride, and the like. The acid halides generally are prepared in situ in the reaction solvent to be utilized for the acylation reaction, for instance, dichloromethane, benzene, toluene, or the like. The acid anhydrides, which are mixed anhydrides, are similarly prepared by standard methods, for instance by reacting a thiophenecarboxylic acid with ketene to form an acetic acid anhydride, or by reaction with an alkanoic acid halide such as propionyl chloride. Active esters, for instance where L is a good leaving group such as pentafluorophenoxy or 1-hydroxybenzotriazole, are readily prepared by reacting the thiophenecarboxylic acid with a hydroxy compound such as pentafluorophenol or 1-hydroxybenzotriazole. The preparation of these thiophene-2-carboxylic acid halides, active esters, and anhydrides are accomplished by routine methodologies commonly utilized in the art of organic chemistry.

Some of the compounds of the invention readily form pharmaceutically acceptable salts when reacted with inorganic and organic acids, for instance hydrochloric acid, sulfuric acid, phosphoric acid, acetic acid, malonic acid, citric acid, para-toluenesulfonic acid, and the like. For example, compounds where X is $(CH_2)_{0-1}$—NR$^1$ and R$^1$ is hydrogen or alkyl readily react with acids to form salts. Similarly, compounds wherein R$^3$ is hydrogen can be reacted with a base such as sodium hydroxide to form a pharmaceutically acceptable salt. Typically, the salts are preferred for oral formulations due to their good aqueous solubility and subsequent favorable bioavailability properties. The invention compounds also form solvates with organic solvents such as methanol or ethanol, as well as with water.

The preparation of the thiophene-2-carboxamidotetrazoles of this invention requires the use of starting materials which are either readily available from commercial sources, or can be synthesized by methods familiar to those skilled in organic chemistry. For instance, the aminotetrazoles are in general commercially available. The thiophene-2-carboxylic acid derivatives are available commercially or are easily synthesized from readily available starting materials. For example, the cyclopentathiophene-2-carboxylic acids and the cyclohexathiophene-2-carboxylic acid (i.e., where X is —CH$_2$— and —CH$_2$CH$_2$—, respectively) can be prepared by reacting a carboxy or thiocarboxy cyclopentanone or cyclohexanone with 2-thioacetic acid to form the corresponding thio ether, and cyclizing the thioether to produce a thiophene-2-carboxylic acid derivative, generally an ester. The ester can be hydrolyzed by normal methods to give the desired thiophene-2-carboxylic acid. The synthesis is depicted by the following scheme:

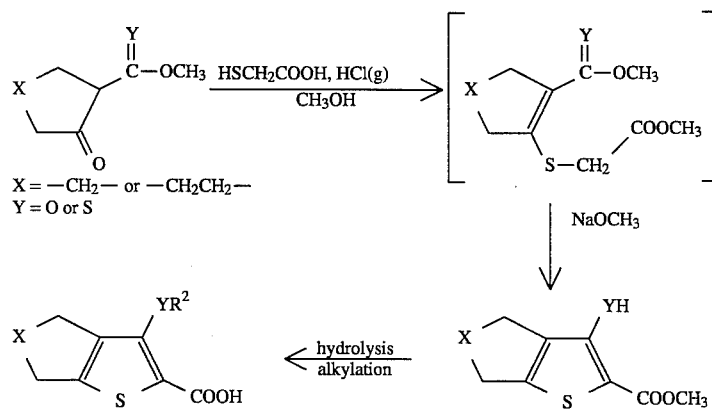

The thienothiophene and thienothiopyran carboxylic acids are similarly prepared from cyclic thio ethers having an oxo group adjacent to a carboxy or thiocarboxy group, for example according to the following scheme:

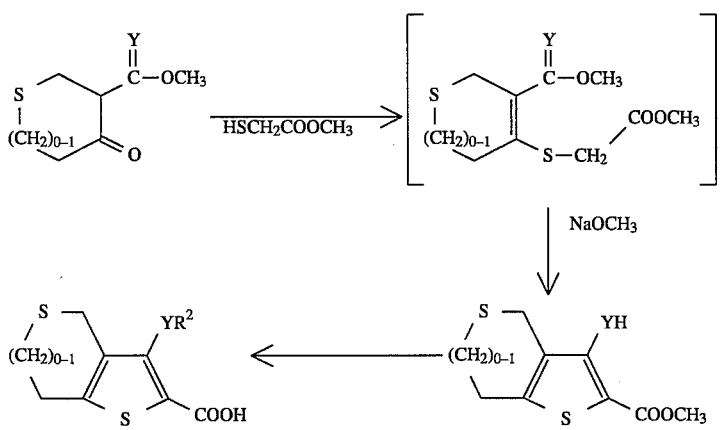

The cyclic thio ethers thus prepared can be oxidized to the corresponding sulfoxides and sulfones by reaction with oxidizing agents such as hydrogen peroxide, m-ochloroperbenzoic acid, or the like.

Compounds of the invention where X is $(CH_2)_{0-1}$—$NR^1$ utilize starting materials which are prepared in a manner similar to that described above. For example, a cyclic amine having an oxo group adjacent to a carboxy or thiocarboxy group is reacted with thioacetic acid to produce the corresponding thio ether, which is then cyclized to the thiophenecarboxylic acid analog. Hydrolysis and alkylation or acylation can be carried out by routine methods. The synthesis is depicted by the following general scheme:

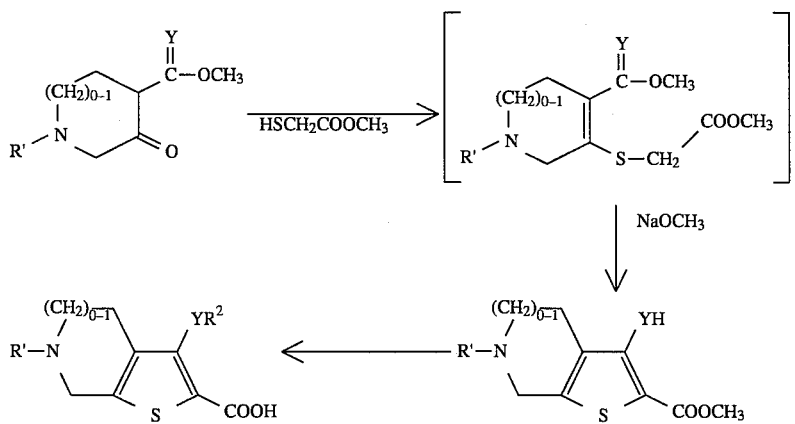

The above reaction is preferably carried out when $R^1$ is a readily removable nitrogen protecting group such as tert-butoxycarbonyl or trimethylsilyl. Mild acid hydrolysis removes the protecting group and provides compounds where $R^1$ is hydrogen, which then can be alkylated or acylated by routine methods. As noted above, the cyclic amines of the invention (i.e., where X=$(CH_2)_{0-1}$—$NR^1$) readily form salts with both organic and inorganic acids.

Representative compounds of the invention include those defined below:

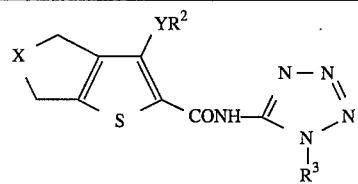

| X | Y | $R^2$ | $R^3$ |
|---|---|---|---|
| $CH_2$ | O | H | H |
| $CH_2CH_2$ | S | H | $CH_3$ |
| $CH_2CH_2$ | S | $CH_3$ | n-butyl |

-continued

[Structure: thiophene fused ring with X, YR² at position 3, CONH-tetrazole (with R³) at position 2]

| X | Y | R² | R³ |
|---|---|-----|-----|
| CH₂CH₂ | S | benzyl | H |
| CH₂CH₂ | O | 3-chlorobenzyl | CH₃ |
| S | O | 4-hydroxyphenyl | CH₂CH₃ |
| S=O | O | H | H |
| SO₂ | S | CH₃ | 3-butenyl |
| -S-CH₂- | S | n-butyl | H |
| -CH₂-S- | O | isopropyl | H |
| -CH₂-S(=O)- | S | 3-aminophenyl | isobutyl |
| -O=S(=O)-CH₂- | S | 3-dimethylaminobenzyl | H |
| HN | O | CH₃ | H |
| CH₃OC(=O)—N | O | Et | H |
| CH₃OC(=O)—N—CH₂- | S | H | H |
| CH₃CH₂C(=O)—N—CH₂- (with O) | S | 2,4,6-trichlorobenzyl | H |
| H—N—CH₂- | S | H | 3-hexynyl |
| n-hexyl—N—CH₂- | S | n-hexyl | isopropyl |
| CH₃—N—CH₂- | S | tert-butyl | H |
| Et—N—CH₂- | S | Et | H |
| -S-CH₂- | O | tert-butyl | n-hexyl |
| -O=S(=O)-CH₂- with O | S | H | 3-hexenyl |
| CH₃—N—CH₂- | S | CH₃ | isopentyl |

The synthesis of the thiophene-2-carboxamidotetrazoles of this invention is further illustrated by the following detailed examples. The examples are intended to be representative only, and are not to be construed as limiting the invention in any respect.

PREPARATION 1

4-[(Diphenoxyphosphinyl)oxy]-2,5-dihydro-3-thiophenecarboxylic acid methyl ester To a solution of 3-carbomethoxytetrahydrothiophene-4-one (Gianturco M. A., Friedel P., Giammarino A. S., *Tetrahedron*, 20:1772 (1964)) (4.0 g, 25 mmol) and triethylamine (6.6 g, 65 mmol) in 50 mL dry THF at 0° was added, over a 15 minute period, diphenylchlorophosphate (17.5 g, 65 mmol). The reaction mixture was stirred at room temperature for 2 days, then treated with ice-cold water and extracted with diethyl ether. The extracts were washed with saturated NaHCO₃, brine, dried with Na₂SO₄, and evaporated to yield an oil (10.6 g).

PREPARATION 2

3-Hydroxy-4,6-dihydro-thieno[3,4-b]thiophene-2-carboxylic acid methyl ester

A solution of the oil from Preparation 1 (4.0 g, 10 mmol), methylthioglycolate (2.65 g, 25 mmol), and N,N-diisopropylethylamine (1.94 g, 15 mmol) in CH$_3$CN (50 mL) was allowed to stand at room temperature 20 hours. The reaction mixture was heated at reflux 2 hours, cooled, treated with cold 2N HCl (75 mL), and extracted with diethyl ether. The extracts were washed with 1N HCl, saturated NaHCO$_3$, brine, and dried with Na$_2$SO$_4$ and evaporated to yield an amorphous tan solid which was added without further purification to a 0.35M solution of NaOMe in MeOH (100 mL) and allowed to stand 16 hours. The reaction mixture was treated with cold 0.5N HCl (285 mL) and extracted with CH$_2$Cl$_2$. The extracts were washed with H$_2$O, brine, dried with MgSO$_4$, and evaporated to yield the title compound as a gold solid (1.95 g), mp 133–137° C.

PREPARATION 3

4-Oxo-tetrahydro-thiopyran-3-carboxylic acid methyl ester

This compound, prepared by the method of Fehnel E. A. and Carmack M., *J. Am. Chem. Soc.*, 70:1814 (1948)), was obtained as a colorless oil (bp 67°–70° C. at 0.28 mm) which crystallizes on standing, mp 58°–61° C.

PREPARATION 4

3-Hydroxy-6,7-dihydro-4H-thieno[3,2-c]thiopyran-2-carboxylic acid methyl ester

The compound from Preparation 3 was treated in the manner described by Donoso R., de Urries P. J., and Lissavetzky J., (*Synthesis*, 526 (1992)) yielding white crystals, mp 86°–89° C. (reference cited reports mp 51°–53° C.), MS (EI) m/e 230 (M+).

PREPARATION 5

4-Methoxycarbonylmethylsulfanyl-1,2,5,6-tetrahydropyridine- 3-carboxylic acid methyl ester monohydrochloride Using the method of Maffrand J-P. and Frehel D., *Bull. Chim. Soc. France II*-48 (1978), 2-mercaptoacetic acid (68.3 g, 0.74 mol) was added to methyl-4-oxo-3-piperidinecarboxylate hydrochloride (71.2 g, 0.37 mol) in dry saturated methanolic HCl (1000 mL) at 0° C. Over the next 4 hours, HCl gas was bubbled in occasionally. The reaction mixture was then stirred at room temperature for 90 hours. The solid was filtered off, washed with diethyl ether, and dried to yield 67 g of white crystals, mp 191°–194° C.

PREPARATION 6

2-Methoxycarbonyl-3-hydroxy-5-tert-butoxycarbonyl-6,7-dihydro-4H-thieno[3,2-C]pyridine To the compound from Preparation 5 (1.41 g, 5.0 mmol) in dioxane (10 mL) -H2O (5 mL) at 0° C. was added 1N NaOH (10 mL) and a solution of di-t-butyl dicarbonate (1.20 g, 5.5 mmol) in dioxane (10 mL). The reaction mixture was stirred at room temperature for 2 hours, diluted with H$_2$O, and extracted with diethyl ether. The extracts were washed with H$_2$O, brine, and dried with Na$_2$SO$_4$. Evaporation yields an oil which was taken up in methanolic KOH (2.9 g 85% KOH in 20 mL dry MeOH) and allowed to stand at room temperature 18 hours. The reaction mixture was poured into ice-water containing HOAc (7 mL) and extracted with diethyl ether. The extracts were washed with saturated NaHCO$_3$, brine, and dried with Na$_2$SO$_4$. Evaporation yields 1.41 g of a colorless oil which, on standing, formed crystals, mp 84.5°–86° C.

PREPARATION 7

3-Hydroxy-5,6-dihydro-4H-cyclopenta[b]thiophene-2-carboxylic acid methyl ester

This compound was prepared from ethyl-2-oxocyclopentanecarboxylate according to the method for Preparation 4. There was obtained 17.1 g of white crystals, mp 73°–75° C.

PREPARATION 8

3-Hydroxy-4,5,6,7-tetrahydro-benzo[b]thiophene-2-carboxylic acid methyl ester

This compound was prepared from ethyl-2-oxocyclohexanecarboxylate according to the method for Preparation 4. There was obtained 4.4 g of white crystals, mp 55°–58° C.

PREPARATION 9

3-Isopropoxy-6,7-dihydro-4H-thieno[3,2-c]thiopyran-2-carboxylic acid

A solution of the compound from Preparation 4 (1.44 g, 6.25 mmol), DBU (1,8-diazabicyclo[5.4.0]undec-7-ene) (1.43 g, 10.6 mmol), and 2-bromopropane (1.31 g, 10.6 mmol) in DMF (20 mL) was heated at 100° C. for 5 hours, then allowed to stand 16 hours at room temperature. The reaction mixture was poured into cold 2N HCl (100 mL) and was extracted with Et$_2$O. The extracts were washed with 0.5N HCl, H$_2$O, brine, dried with Na$_2$SO$_4$, and evaporated.

The oil residue was taken up in MeOH and 2.4N LiOH (15 mL) and was heated on a steam bath for 20 minutes. The reaction mixture was treated with dilute HCl and was extracted with Et$_2$O. The extracts were washed with H$_2$O, brine, dried with MgSO$_4$, and evaporated to dryness. The residue was recrystallized from Et$_2$O/n-hexane to yield 1.17 g of pale tan crystals, mp 148°–149° C.

PREPARATION 10

3-Isopropoxy-5,6-dihydro-4H-cyclopenta[b]thiophene-2-carboxylic acid

This compound was prepared from the compound in Preparation 7 according to the method for Preparation 9. There was obtained 6.13 g of white crystals, mp 133°–135.5° C.

PREPARATION 11

3-Isopropoxy-4,5,6,7-tetrahydro-benzo[b]thiophene-2-carboxylic acid

This compound was prepared from the compound in Preparation 8 according to the method for Preparation 9. There was obtained 2.5 g of white crystals, mp 118.5°–120.5° C.

PREPARATION 12

3-Isopropoxy-4,6-dihydro-thieno[3,4-b]thiophene-2-carboxylic acid

This compound was prepared from the compound in Preparation 2 according to the method for Preparation 9. There was obtained 1.05 g of a gummy solid which was used without further purification.

PREPARATION 13

3-Isopropoxy-5-oxo-6,7-dihydro-4H-thieno[3,2-c]thiopyran- 2-carboxylic acid

3-Isoproxy-6,7-dihydro-4H- thieno [3,2-c]thiopyran-2-carboxylic acid from Preparation 9 (1.16 g, 4.5 mmol) was dissolved in HOAc (25 mL) and 31.5% aqueous H$_2$O$_2$ (0.49 g) was added. After standing 20 hours at room temperature, an additional 5 drops of H$_2$O$_2$ was added to complete the reaction. After 2 more hours, the reaction mixture was concentrated to dryness by evaporation of the solvents, and the residue was recrystallized from EtOAc-MeOH to yield 0.92 g of pale tan crystals, mp 192°–193° C.

PREPARATION 14

2-Methoxycarbonyl-3-isopropoxy-5-tert-butoxycarbonyl-6,7-dihydro-4H-thieno[3,2-c]pyridine To a solution of 10.96 g (0,035 mol) of 2-methoxycarbonyl- 3-hydroxy-5-tert-butoxycarbonyl-6,7-dihydro-4H-thieno[3,2-c]pyridine (prepared as described in Preparation 6) in 125 mL of tetrahydrofuran were added 8.14 g (0.0535 mol) of DBU (1,8-diazabicyclo[5.4.0]undec-7-ene and 6.55 g (0.053 mol) of 2-bromopropane. The solution was heated at reflux for 4 hours. An additional 3.28 g (0.0266 mol) of 2-bromopropane and 4.07 g (0.0268 mol) of DBU dissolved in 75 mL of DMF were added, and the reaction mixture was stirred at 82° C. for 2.5 hours, cooled to 24° C., and stirred for 3 days. The reaction mixture was added to 550 g of ice water containing 10 mL of glacial acetic acid. The aqueous mixture was extracted four times with 100 mL portions of diethyl ether. The ethereal extracts were combined, washed with saturated aqueous sodium bicarbonate, with water and brine, dried over sodium sulfate, and the solvent was removed by evaporation under reduced pressure to afford 13 g of crystalline 2-methoxycarbonyl-3-isopropoxy-5-tert-butoxycarbonyl-6,7-dihydro-4H-thieno[3,2-c]pyridine, mp 76°–81° C.

PREPARATION 15

3-Isopropoxy-5-tert-butoxycarbonyl-6,7-dihydro-4H-thieno[3,2-c]pyridine-2-carboxylic acid The methyl ester compound prepared in Preparation 14 (6.40 g, 0.018 mol) was dissolved in a mixture of 100 mL of methanol and 100 mL of 1N sodium hydroxide. The solution was heated on a steam bath for 2 hours. The reaction solution was added to 100 g of ice containing 10 mL of glacial acetic acid, and the aqueous mixture was extracted three times with 100 mL portions of diethyl ether. The ethereal extracts were combined, washed with water, brine, and dried over sodium sulfate. The solvent was removed by evaporation to give an oil, which was crystallized from 30 mL of diethyl ether to yield 4.51 g of 3-isopropoxy-5-tert-butoxycarbonyl- 6,7-dihydro-4H-thieno[3,2-c]pyridine-2-carboxylic acid, mp 128°–129° C.

EXAMPLE 1

3-Isopropoxy-4,5,6,7-tetrahydro-benzo[b]thiophene-2-carboxylic acid (1H-tetrazol-5-yl)-amide The compound from Preparation 11 (0.72 g, 3.0 mmol) and 1,1'-carbonyldiimidazole (0.9 g, 5.55 mmol) were taken up in DMF (5 mL) and heated at 80° C. for 20 minutes. When imidazolide formation was complete, 5-aminotetrazole (0.55 g, 6.5 mmol) was added, and the mixture was heated at 85° C. for 5 hours, then allowed to stand at room temperature 18 hours. The reaction mixture was diluted with Et$_2$O, and the solid was filtered off. The solid was taken up in CH$_2$Cl$_2$, and the resulting solution was washed with 2N HCl, H$_2$O, brine, and dried with MgSO$_4$. After concentration to a small volume, Et$_2$O was added, and the precipitated solid was collected and recrystallized from MeOH to provide 0.42 g of white crystals, mp 223°–225° C.

EXAMPLE 2

3-Isopropoxy-5,6-dihydro-4H-cyclopenta[b]thiophene-2-carboxylic acid (1H-tetrazol-5-yl)-amide This compound was prepared from the compound in Preparation 10 according to the method of Example 1. There was obtained 0.78 g of a white solid, mp 242.5°–245° C.

EXAMPLE 3

3-Isopropoxy-4,6-dihydro-thieno[3,4-b]thiophene-2-carboxylic acid (1H-tetrazol-5-yl)-amide This compound was prepared from the compound in Preparation 12 according to the method for Example 1. There was obtained 0.066 g of tan crystals, mp 235°–236° C.

EXAMPLE 4

3-Isopropoxy-6,7-dihydro-4H-thieno[3,2-c]thiopyran-2-carboxylic acid (1H-tetrazol-5-yl)-amide This compound was prepared from the compound in Preparation 9 according to the method for Example 1. There was obtained 0.057 g of tan crystals, mp 223°–234° C.

EXAMPLE 5

3-Isopropoxy-5-oxo-6,7-dihydro-4H-thieno [3,2-c]thiopyran-2-carboxylic acid (1H- tetrazol-5-yl)-amide To a stirred solution of 0.494 g (1.8 mM) of 3-isopropoxy-5-oxo-6,7-dihydro-4H-thieno[3,2-c]thiopyran-2-carboxylic acid (from Preparation 13) in 10 mL of DMF were added 0.438 g (2.7 mmol) of 1,1'-carbonyldiimidazole. The reaction mixture was heated at 80° C. for 60 minutes, followed by addition in one portion of 0.283 g (3.33 mmol) of 5-aminotetrazole. The reaction mixture was heated at 80° C. for 5 hours, cooled to 24° C., and stirred for an additional 18 hours. The mixture was concentrated to dryness by evaporation of the solvent under reduced pressure. The residue was dissolved in 100 mL of chloroform, washed with 2N HCl, water, brine, dried over MgSO$_4$, and the solvent was removed by evaporation under reduced pressure. The solid residue was recrystallized from methanol/diethyl ether to afford 0.279 g of 3-isopropoxy-5-oxo-6,7-dihydro-4H-thieno[3,2-c]thiopyran-2-carboxylic acid (1H-tetrazol-5-yl) amide, mp 225°–226° C.

EXAMPLE 6

3-Isopropoxy-5,5-dioxo-6,7-dihydro-4H-thieno[3,2-c]thiopyran-2-carboxylic acid (1H-tetrazol-5-yl) amide To a stirred solution of 0.2 g (0.59 mmol) of 3-isopropoxy-5-oxo-6,7-dihydro-4H-thieno[3,2-c]thiopyran-2-carboxylic acid (1H-tetrazol-5-yl)amide (from Example 5) in 15 mL of glacial acetic acid was added in one portion 0.19 g of 31.5% aqueous hydrogen peroxide. The reaction mixture stood at 24° C. for 3 days, and then was treated with 10% aqueous sodium metabisulfite. The solvent was removed by evaporation under reduced pressure to give a solid residue. The solid was crystallized from 20 mL of ethylacetate and 1 mL of water to provide 0.115 g of 3-isopropoxy-5,5-dioxo-6,7-dihydro-4H-thieno[3,2-c]thiopyran-2-carboxylic acid (1H-tetrazol-5-yl) amide, mp 230°–232° C.

EXAMPLE 7

3-Isopropoxy-5-tert -butoxycarbonyl-6,7-dihydro-4H-thieno[3,2-c]pyridine-2-carboxylic acid (1H-tetrazol-5-yl)amide To a stirred solution of 1.43 g (4.2 mmol) of 3-isopropoxy-5-tert-butoxycarbonyl-6,7-dihydro-4H-thieno[3,2-c]pyridine-2-carboxylic acid in 15 mL of DMF were added 1.07 g (6.6 mmol) of 1,1'-carbonyldiimidazole. The reaction mixture was heated at 85° C. for 2 hours. 5-Aminotetrazole (0.655 g, 7.7 mmol) was added to the reaction mixture in one portion, and the mixture was stirred at 85° C. for 8 hours. The solution was cooled to 24° C. and stirred at that temperature for 18 hours. The reaction mixture was diluted by addition of 100 mL of water and was extracted three times with 50 mL portions of chloroform. The extracts were washed with 50 mL of 2N HCl, water, brine, dried over $Na_2SO_4$, and concentrated to dryness by evaporation of the solvent under reduced pressure. The residue was crystallized from 500 mL of diethyl ether to give 1.02 g of 3-isopropoxy-5-tert-butoxycarbonyl-6,7-dihydro-4H-thieno[3,2-c]pyridine-2-carboxylic acid (1H-tetrazol-5-yl) amide, mp 189°–191° C.

EXAMPLE 8

3-Isopropoxy-6,7-dihydro-4H-thieno[3,2-c]pyridine-2-carboxylic acid (1H-tetrazol-5-yl)amide hydrochloride A solution of 0.10 g (0.245 mmol) of 3-isopropoxy-5-tert-butoxycarbonyl-6,7-dihydro-4H-thieno[3,2-c]pyridine-2-carboxylic acid (1H-tetrazol-5-yl) amide (from Example 7) in 15 mL of 5% (w/w) hydrogen chloride in methanol was stirred at 24° C. for 3 days. The reaction solvent was removed by evaporation under reduced pressure to afford an oil. The oil was crystallized from 10 mL of ethyl acetate/diethyl ether (1:1 v/v) to afford 0.089 g of 3-isopropoxy-6,7-dihydro-4H-thieno[3,2-c]pyridine-2-carboxylic acid (1H-tetrazol-5-yl) amide monohydrochloride, mp 237°–238° C.

The thiophene-2-carboxamidotetrazoles described above have been found to inhibit the leukocyte adhesion molecule Mac-1, and thereby are useful as cytoprotective agents to treat and prevent diseases mediated by the Mac-1 integrin. Cytoprotection as used herein includes protection against damage to the gastrointestinal mucosa by the blockage of prostaglandin biosynthesis.

The role of endothelial adhesion molecules such as Mac-1 has been implicated in a number of human disease states. For example, neutrophil-mediated inflammation has been established as involved in adult respiratory distress syndrome, multi-organ failure, and reperfusion injury. One way to inhibit or treat such inflammatory responses entails competitively blocking the adhesive interactions between neutrophils and the endothelium adjacent to the inflamed region (see Watson, et al., *Nature*, 349:164–167 (1991)). We have now discovered that the thiophene-2-carboxamidotetrazoles of this invention are effective at blocking the Mac-1 leukocyte adhesion molecule.

Studies have established that neutrophil adherence to the vascular endothelium is a critical early event in the pathogenesis of gastric mucosal injury induced by nonsteroidal anti-inflammatory drugs (NSAIDs) (see Wallace, et al., *Am. J. Physiol.*, 265:G993–G998 (1993)), incorporated herein by reference. A preferred embodiment of this invention is thus treatment of NSAID-induced gastrointestinal lesions and ulcers comprising administering to a subject in need of treatment an amount of a thiophene-2-carboxamidotetrazoles of this invention effective to inhibit Mac-1 adhesion. Shappell, et al., in *J. of Immunology*, 144:2702–2711 (1990), incorporated herein by reference, established that the Mac-1 leukocyte integrin mediates the adherence-dependent production of hydrogen peroxide, and that inhibition of such adhesion is a viable treatment for myocardial ischemia-reflow injury and results in reduction in infarct size. Another preferred embodiment of this invention is therefore a method of treating ischemia and reperfusion comprising administering to a subject in need of treatment a Mac-1 inhibiting amount of a thiophene-2-carboxamidotetrazoles of this invention.

Similarly, Simpson, et al., in *Circulation*, 81:226–237 (1990), incorporated herein by reference, confirms that inhibition of Mac-1 adhesion significantly reduces myocardial ischemia. Accordingly, this invention provides a method of treating myocardial ischemia by administering an effective amount of a thiophene-2-carboxamidotetrazole. Mulligan, et al., *J. of Immunology*, 150:2401–2406 (1993), incorporated herein by reference, disclose that inhibition of Mac-1 can diminish the effects of lung injuries resulting from acute inflammatory reactions. The invention therefore provides a method of treating lung disease mediated by Mac-1 by administering to a subject in need of treatment a Mac-1 inhibiting amount of a thiophene-2-carboxamidotetrazole.

We have evaluated the ability of the thiophene-2-carboxamidotetrazoles to inhibit Mac-1 adhesion in in vitro and in vivo models recognized and routinely utilized by those skilled in the art. For example, Wallace, et al., *Gastroenterology*, 100:878–883 (1991), describes in vivo studies to measure prevention of adherence of leukocytes to vascular endothelium mediated by several adhesion molecules, one of which is Mac-1. Similarly, Rosen, *J. Leukocyte Biology*, 45:465–469 (1990), incorporated herein by reference, discusses in vivo testing in mice, rabbits, and dogs for determining leukocyte adhesion and inflammatory recruitment.

Protocol for Human Neutrophil Mac-1 Adhesion Assay

We evaluated several invention compounds utilizing methodology similar to that of Ferrante and Thong as described in *J. Immunol. Methods*, 24:389–393 (1978), and Shappell, et al., *J. Immunol.*, 144:2702–2711 (1990), both of which are incorporated herein by reference. Namely, we utilized Ferrante and Thong's methodology to isolate neutrophils from ethylenediaminetetraacetic acid (EDTA)-treated venous blood obtained from healthy human volunteers. Keyhole limpet hemocyanin (KLH) coated microtiter plates were prepared as follows:

All pipetting was automated using the Cetus Pro/Pette (Perkin-Elmer; division of Applied Biosystems, Foster, Calif.). KLH, Megathura crenulata; Calbiochem-Novabiochem, La Jolla, Calif., was prepared at a concentration of 0.5 mg/mL in Dulbecco's PBS phosphate buffered saline (PBS) with $Ca^{++}$, pH 7.2 (DPBS).

Microtiter plates are prewashed with 50% EtOH for 1 hour at 37° C., then drained and blotted to dryness. Then 0.3 mL KLH solution was pipetted into each well of the 96 well microtiter plate, covered and incubated overnight at 37° C. Plates are then inverted to drain, blotted to dryness, washed with 0.3 mL cold D-PBS, drained, blotted to dryness, then stored at 4° C. until use. Procedure for PMN KLH (Mac-1 Adhesion Assay)

On the Pro/Pette system, a treatment plate was placed in plate position 1 (P-1), buffer Micro.trof was placed in plate position 2 (P-2), and a single row of tips in a spare magazine are placed in the tip position on the carriage. Two hundred ten µL aliquots D-PBS are pipetted into all wells (105 µL using Cetus File #18, Micro.trof 3, no mixes, tip row H, no tip change, run twice). Drug plate was placed in plate position 2 (P-2). Donor drug plates were prepared to contain buffer or drug in appropriate wells. Thirty µL drug or D-PBS buffer are pipetted into appropriate wells in the treatment plate in position 1 (P-1) (Cetus File #17, one mix before and after, changing tips) from donor plate. Thirty μL of neutrophils (PMNs) (30 μL of $10^7$ cells/mL) were next pipetted from either a Micro.trof 1, position 2 (P-2), or a row of 0.5 mL capacity microcentrifuge tubes (Sarstedt RIA vials) to plate 1 using Cetus File #18, changing tips, one mix (50 μL) before and after. Cells and drug were then incubated for 10 minutes at 37° C. Agonist (e.g., FMLP) or D-PBS buffer (30 μL) were next pipetted to appropriate wells using Cetus File #18 (Micro.trof) or Cetus File #42 (for plate to plate), changing tips and one mix before and after. Cell/drug/agonist mixture was then incubated for 60 minutes at 37° C. After the incubation period, the treatment plate is gently inverted to drain, blotted lightly to dryness on a paper towel. The treatment plate is then washed with 300 μL D-PBS buffer using Cetus File #18, using pump at slow speed, again inverted to drain, and again blotted to dryness. Adherent cells are stained by the addition of 150 μL D-PBS buffer to all wells, using Cetus File #18, Micro.trof 3 no tip change. Then the addition of 150 μL of 0.025% Rose Bengal dye in D-PBS, again using Cetus File #18, Micro.trof 3 no tip change. The treatment plate is then incubated overnight at 37° C.

After overnight incubation, the treatment plate is gently inverted to drain, blotted to dryness on paper towel, then gently washed with 300 μL D-PBS buffer using Cetus File #18, using pump at slow sped. The treatment plate is then gently inverted to drain, and blotted to dryness. The washing of the treatment plate is repeated until all excess dye is removed.

To develop the dye color, 150 μL 50% EtOH is added to each well of the treatment plate using Cetus File #18, Micro.trof 3, no mixes, no tip change. The treatment plate is then covered and incubated for 60 minutes at 37° C. After the incubation, 150 μL 50% EtOH is added to each well of the treatment plate using Cetus File #18, Micro.trof 3, mixing three times, changing tips. Optical densities (ODs) for the wells of the treatment plate are read using a Titertek Multiskan(R) MCC/340 microtiter plate reader with absorbance wavelength 570 nm (Rose Bengal), then data is either read from a thermal printout tape or sent directly to a Lotus 123 file. Data Calculations (Lotus 123 spreadsheet):

a. mean unstimulated cell control OD is determined and subtracted from all other values b. mean net stimulated, e.g., FMLP, control values are determined c. mean drug values are determined and percent drug inhibition vs. stimulus control are calculated as follows:

Percent Inhibition =

$$\frac{OD \text{ stimulated control} - OD \text{ unstimulated control}) - (OD \text{ treated} - OD \text{ unstimulated control})}{(OD \text{ stimulated control} - OD \text{ unstimulated control})} \times 100$$

d. $IC_{50}$ determinations, plotting logdose vs. percent inhibition, are determined by linear regression analysis using the least squares method.

The following table presents MAC-1 inhibitory activity for representative compounds of this invention.

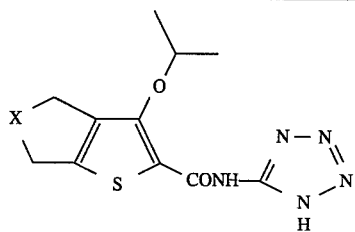

| Example | X | MAC-1 $IC_{50}$ μM |
|---|---|---|
| 1 | $CH_2CH_2$ | 1.5 |
| 2 | $CH_2$ | 27% @ 33 μM |
| 3 | S | 1.2 |
| 4 | $SCH_2$ | 3.0 |
| 5 | $SOCH_2$ | 22.7 |
| 6 | $SO_2CH_2$ | 38% @ 33 μM |
| 7 | $BOCNCH_2$ | 21.2 |
| 8 | $HCl.NHCH_2$ | 4.3 |

The foregoing data establish that the thiophene-2-carboxamidotetrazoles of this invention effectively inhibit Mac-1 mediated diseases such as inflammatory gastritis and ulceration, ischemia, reperfusion, ulcerative colitis, inflammatory bowel disease, and multiple sclerosis. Accordingly, the compounds can be employed as pharmaceuticals. In a further embodiment of the invention, pharmaceutical formulations comprising the invention compounds are provided. The compounds can be formulated with standard pharmaceutical excipients, carriers and diluents for convenient administration via the oral or parenteral routes. For oral administration, the compounds will be formulated into solid or liquid preparations such as tablets, capsules, solutions, suspensions, or sustained release compositions with polymers, oils, waxes, and the like. Typical formulations will contain about 10% to about 90% of the thiophene-2-carboxamidotetrazole by weight. For parenteral administration, the compounds will be made into solutions or suspensions by admixing with carriers such as water, isotonic saline, 5% aqueous glucose, ethanol, mineral oil, propylene glycol, polyethylene glycol, and the like. The compounds can also be formulated as creams, lotions, and patches for transdermal administration. The compounds will be administered at doses which are effective to inhibit Mac-1 adhesion, and are thus effective to treat the disease mediated thereby, such as NSAID-induced gastrointestinal lesions and ulcers. Typical doses for such treatments will be from about 0.5 to about 500 mg per kg of body weight, and ideally from about 1 to about 100 mg/kg. The formulations can be in unit dosages for convenient administration from 1 to 4 times a day as needed. The compounds can be employed prophylactically to inhibit Mac-1 adhesion and thus prevent formation of inflammatory disorders such as NSAID-induced gastrointestinal lesions and ulcers.

The following examples further illustrate the pharmaceutical formulations provided by the invention and the use of the compounds.

EXAMPLE 9

| Formulation of Oral Suspension | |
|---|---|
| Ingredient | Amount |
| 3-Benzyloxy-4,5,6,7-tetrahydro-benzo[b]thiophene-2-carboxylic acid (1H-tetrazole-5-yl)-amide | 2500 mg |
| Sorbital solution (70% N.F.) | 40 mL |
| Sodium benzoate | 100 mg |
| Saccharin | 10 mg |
| Orange flavoring | 50 mg |
| Distilled water q.s. | 100 mL |

The sorbitol solution is added to 40 mL of distilled water and the thiophenecarboxamidotetrazole is suspended therein. The remaining ingredients are added and dissolved. The volume is adjusted to 100 mL with distilled water. Each mL of syrup contains 25 mg of active ingredient.

EXAMPLE 10

| Preparation of Capsule | |
|---|---|
| Ingredient | Amount |
| 3-Tert-butylthio-4,6-dihydro-thieno[3,4-b]thiophene-2-carboxylic acid (1H-tetrazole-5-yl)-amide | 250 mg |
| Lactose | 150 mL |
| Starch | 100 mg |
| | 500 mg |

The ingredients are blended to uniformity and encapsulated into gelatin capsules. Such capsules are administered at the rate of one to three each day for treating inflammatory bowel disease and ulcerative colitis.

EXAMPLE 11

| Preparation of IV Solution | |
|---|---|
| Ingredient | Amount |
| 3-(4-aminophenoxy)-6,7-dihydro-4H-thieno[3,2-c]pyridine-2-carboxylic acid (1H-tetrazole-5-yl)-amide hydrochloride | 600 mg |
| Isotonic saline | 1000 mL |

The invention compound is dissolved in the isotonic saline under sterile conditions. The solution is administered IV to a subject suffering from ischemia or reperfusion.

We claim:

1. A compound of the formula

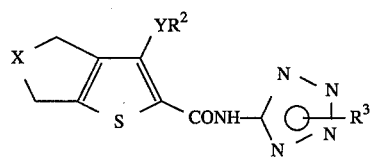

wherein:

X is $(CH_2)_{1-2}$,

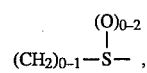

and $(CH_2)_{0-1}$—$NR^1$, where $R^1$ is hydrogen, $C_1$–$C_6$ alkyl, $C_1$–$C_6$ alkanoyl, or $C_1$–$C_6$ alkoxycarbonyl;

Y is O or S;

$R^2$ is $C_1$–$C_6$ alkyl or $(CH_2)_{0-1}Ar$, where Ar is phenyl or phenyl substituted with one, two, or three groups selected from halo, $C_1$–$C_6$ alkyl, hydroxy, $C_1$–$C_6$ alkoxy, nitro, amino, $C_1$–$C_6$ alkylamino, and di-$C_1$–$C_6$ alkylamino;

$R^3$ is hydrogen, $C_1$–$C_6$ alkyl, $C_2$–$C_6$ alkenyl, and $C_2$–$C_6$ alkynyl;

and the pharmaceutically acceptable acid addition salts and solvates thereof.

2. A compound of claim 1 wherein $R^3$ is hydrogen.
3. A compound of claim 2 wherein $R^2$ is $C_1$–$C_6$ alkyl.
4. A compound of claim 3 wherein Y is O.
5. A compound of claim 4 wherein X is —$CH_2$—, said compound being 3-isopropoxy-5,6-dihydro-4H-cyclopenta[b]thiophene-2-carboxylic acid (1H-tetrazol-5-yl)-amide.
6. A compound of claim 4 wherein X is —$CH_2$—$CH_2$—, said compound being 3-isopropoxy-4,5,6,7-tetrahydrobenzo[b]thiophene-2-carboxylic acid (1H-tetrazol-5-yl)-amide.
7. A compound of claim 4 wherein X is

8. A compound of claim 7 wherein X is —S—.
9. The compound of claim 8 which is 3-isopropoxy-4,6-dihydro-thieno[3,4-b]thiophene-2-carboxylic acid (1H-tetrazol-5-yl)-amide.
10. The compound of claim 8 which is 3-isopropoxy-6,7-dihydro-4H-thieno[3,2-c]thiopyran-2-carboxylic acid (1H-tetrazol-5-yl)-amide.
11. A compound of claim 4 wherein X is

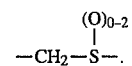

12. The compound of claim 11 which is 3-isopropoxy-5-oxo-6,7-dihydro-4H-thieno[3,2-c]thiopyran-2-carboxylic acid (1H-tetrazol-5-yl)-amide.
13. The compound of claim 11 which is 3-isopropoxy-5,5-dioxo-6,7-dihydro-4H-thieno[3,2-c]thiopyran-2-carboxylic acid (1H-tetrazol-5-yl)-amide.
14. A compound of claim 4 wherein X is $(CH_2)_{0-1}$—$NR^1$.
15. A compound of claim 14 wherein $R^1$ is hydrogen.
16. A compound of claim 15 wherein X is —$NR^1$—.

17. A compound of claim 15 wherein X is —CH₂—NR¹—.

18. The compound of claim 17 which is 3-isopropoxy-6,7-dihydro-4H-thieno[3,2-c]pyridine-2-carboxylic acid (1H-tetrazol-4-yl)amide hydrochloride.

19. The compound of claim 14 which is 3-isopropoxy-5-tert-butoxycarbonyl-6,7-dihydro-4H-thieno[3,2-c]pyridine-2-carboxylic acid (1H-tetrazol-5-yl)amide.

20. A pharmaceutical formulation comprising a compound of claim 1 together with a pharmaceutically acceptable diluent, excipient, or carrier therefor.

21. A formulation of claim 20 employing a compound wherein R³ is hydrogen, Y is 0, and R² is C₁-C₆alkyl.

22. A formulation of claim 21 employing a compound wherein X is —CH₂— or —CH₂CH₂—.

23. A formulation of claim 21 employing a compound wherein X is

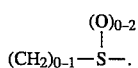

24. A formulation of claim 21 employing a compound wherein X is (CH₂)₀₋₁—NR¹—.

25. A method of providing cytoprotection to an animal by inhibiting the integrin Mac-1 comprising administering to a subject a Mac-1 inhibiting amount of a compound of claim 1.

26. The method of treating NSAID-induced gastritis in an animal comprising administering to the animal an NSAID-induced gastritis inhibiting amount of a compound of claim 1.

27. The method of treating inflammation in an animal comprising administering to the animal an antiinflammatory amount of a compound of claim 1.

28. The method of treating inflammatory bowel disease in an animal comprising administering to the animal an inflammatory bowel disease inhibiting amount of a compound of claim 1.

* * * * *